(12) United States Patent
Klyosov et al.

(10) Patent No.: US 6,914,055 B2
(45) Date of Patent: *Jul. 5, 2005

(54) DELIVERY OF A THERAPEUTIC AGENT IN A FORMULATION FOR REDUCED TOXICITY

(76) Inventors: Anatole Klyosov, 36 Walsh Rd., Newton, MA (US) 02459; David Platt, 12 Appleton Cir., Newton, MA (US) 02459

(*) Notice: Subject to any disclaimer, the term of this patent is extended or adjusted under 35 U.S.C. 154(b) by 0 days.

This patent is subject to a terminal disclaimer.

(21) Appl. No.: 10/649,130

(22) Filed: Aug. 27, 2003

(65) Prior Publication Data

US 2004/0038935 A1 Feb. 26, 2004

Related U.S. Application Data

(62) Division of application No. 09/818,596, filed on Mar. 27, 2001, now Pat. No. 6,645,946.

(51) Int. Cl.[7] .................. A01N 43/04; A61K 31/70; A61K 31/715; A61K 31/505
(52) U.S. Cl. .................. 514/54; 514/23; 514/34; 514/256; 514/974
(58) Field of Search .................. 514/23, 34, 54, 514/256, 974

(56) References Cited

U.S. PATENT DOCUMENTS

| 5,118,673 A | * | 6/1992 | Carpenter et al. ............ 514/54 |
| 5,773,425 A | * | 6/1998 | McAnalley et al. .......... 514/54 |
| 5,786,342 A | * | 7/1998 | Carpenter et al. ............ 514/54 |
| 5,834,442 A | * | 11/1998 | Raz et al. ..................... 514/54 |
| 5,861,142 A | * | 1/1999 | Schick ......................... 424/61 |

OTHER PUBLICATIONS

Ouchi et al., "Synthesis and Cytotoxic Activity of Oxidized Galactomannan/ADR Conjugate", J.M.S. Pure Applied Chemistry, 1997, A34(6), pp. 975–989.*

* cited by examiner

Primary Examiner—James O. Wilson
Assistant Examiner—Traviss C. McIntosh, III
(74) Attorney, Agent, or Firm—Stephen J. Gaudert; Perkins, Smith & Cohen, LLP

(57) ABSTRACT

Methods and compositions for reducing toxicity of a toxic agent are provided in which a polysaccharide, galactomannan is coadministered with a therapeutic agent in a liquid formulation to a subject to reduce toxicity of the agent for the subject.

10 Claims, No Drawings

DELIVERY OF A THERAPEUTIC AGENT IN A FORMULATION FOR REDUCED TOXICITY

RELATED APPLICATIONS

This Divisional application claims priority to and the benefit of U.S. patent application Ser. No. 09/818,596, filed Mar. 27, 2001, now U.S. Pat. No. 6,645,946.

FIELD OF THE INVENTION

Methods and compositions are provided that relate to the administration of a toxic agent to a subject in a formulation in which toxicity is substantially reduced.

BACKGROUND

Many therapeutic agents typified by chemotherapeutics are effective at treating a particular condition, but may at the same time have toxic side effects for the patients that significantly impact the quality of life for the patient. These toxic side effects may arise through the biological action of the agents. For example, a majority of chemotherapy agents kill cancer cells by acting on cells that are actively dividing and replicating. These agents unfortunately do not discriminate between cancer cells and actively dividing normal cells such as blood cells forming bone marrow, cells in the digestive tract, hair follicles, and reproductive cells. Because the chemotherapeutic agents are toxic, the effectiveness of the drug is limited because dosage levels and treatment frequency cannot exceed tolerance levels for non-cancerous cells. Moreover, the chemotherapy regimen often dramatically diminishes the quality of a patient's life through its physical and emotional side effects.

In attempts to overcome the problems of toxicity, chemotherapeutic agents have been targeted to tumor cells by covalently binding the agent to a carrier macromolecule that binds a specific receptor on the surface of a target cell. The carrier molecule is commonly a protein or glycoprotein but may also be a carbohydrate. Limitations of this approach include the ability of the conjugate to effectively and selectively bind the drug target.

An alternative approach to treating patients is to search for therapeutic agents that act on targets that are only associated with diseased tissue. For example, certain cancer drugs are being developed that inhibit angiogenesis, an activity that is essential for growth of a tumor but not otherwise essential in an adult subject except for wound healing or during the menstrual cycle. Another approach is to inhibit tumor metastasis. Potential anti-metastatic agents include a class of modified citrus pectins which are polysaccharides that prevent metastasis of primary tumors by acting as antagonists for growth factors that interact with cell receptors to prevent metastasized cells from lodging at a secondary site (Platt et al. J. Natl Cancer Inst. 84, 438–442 (1992); U.S. Pat. No. 5,801,002, Raz, U.S. Pat. No. 5,895, 784). Carbohydrate binding proteins have also been used to prevent metastasis of tumors. These compounds are galactose specific carbohydrate binding proteins that bind to galactose binding sites on metastatic cells and interfere with cell-cell interactions necessary during metastasis. (Platt: U.S. Pat. No. 5,681,923). Simple sugars such as methyl-∀-D lactoside and lacto-N-tetrose have been shown to inhibit metastasis of B16 melanoma cells, while D-galactose and arabinogalactose inhibited liver metastasis of L-1 sarcoma cells (Beuth et al. J. Cancer Res. Clin. Oncol. 113, 51, 1987).

Despite the increasing resources applied to develop new therapies for cancer, survival rates for most cancer patients have not materially improved over the last 15 years (American Cancer Society, 1995 "Cancer Facts & Figures"). In most cases, particularly when a tumor is not detected at an early stage, cancer chemotherapy merely partially prolongs a patient's life, often for only a few months. Given the rigors of repeated chemotherapeutic treatments, and taking into account the low response rates and the modest effects on survival time, significant toxicity and side effects which reduce the patient's quality of life have become a major issue. Increasing efficacy of a drug can be translated into decreasing of the dosage of the drug, and decreasing its toxicity. Further, decreasing of toxicity per se leads to improvement of the patient's quality of life.

However effective a therapeutic agent may be in modifying an abnormal biological condition, undesirable toxic side-effects impinge on the optimum use of the agents.

SUMMARY OF THE INVENTION

In an embodiment of the invention, a method is provided for delivering an effective dose of a therapeutic agent to a subject in a formulation that reduces the toxic side effects of the agent that includes the step of providing a polysaccharide, for example a galactomannan, combining the polysaccharide with the effective dose of the agent to form a mixture; and administering the mixture to the subject. The agent may be a chemotherapeutic agent. Moreover, the mixture may be administered parenterally.

In a further embodiment, a method is provided for treating a cancer in a subject, comprising: administering parenterally an effective dose of a chemotherapeutic agent in a mixture with an effective dose of a galactomannan.

An example of a galactomannan is a polysaccharide having a size is in the range of 20,000–600,000 D or in the range of 90,000 to 415,000 D or in the range of 40,000–200, 000 D. In specific examples, the galactomannan may have an average size of 83,000 D or 215,000 D. In a further embodiment of the invention, the galactomannan is isolated from an isolate from *Gleditsia triacanthos*. In a further embodiment, a hydrolysis product of the galactomannan is obtained which is has a lower molecular weight than the isolated non-modified form. In other embodiments of the invention, a galactomannan is obtained which is a derivative of an isolate from *Medicago falcata*.

In embodiments of the invention, a galactomannan is used to reduce toxicity of a therapeutic agent when it is mixed with the agent prior to administration. The galactomannan may be a ∃1,4 D-galactomannan. Moreover, the galactomannan may include a ratio of 2.0–3.0 mannose to 0.5–1.5 galactose. The ratio of mannose to galactose may be 2.6 mannose to 1.5 galactose or 2.2 mannose to 0.9 galactose or 1.13 mannan to 1 galactose or 2.2 mannose to 1 galactose.

The ratio of galactomannan to chemotherapeutic agent in the mixture may be in the range of 0.1:1 w/w to 10:1 w/w. In an embodiment of the invention, the mixture has a reduced toxicity of greater than 50% compared with the same dose of the agent absent galactomannan. The mixture may have a reduced toxicity of greater than 80% compared with the same dose of the agent absent galactomannan.

In an embodiment of the invention, the therapeutic agent is a chemotherapeutic agent, for example, adriamycin or 5-Fluorouracil (5-FU).

A further embodiment of the invention provides a method for use in treating a cancer including any of chronic leukemia, breast cancer, sarcoma, ovarian carcinoma, rectal cancer, throat cancer, melanoma, colon cancer, bladder cancer, lung cancer, mammary adenocarcinoma, gastrointestinal cancer, stomach cancer, prostate cancer, pancreatic cancer, or Kaposi's sarcoma.

In an embodiment of the invention, a cancer therapeutic formulation with reduced toxicity includes an effective dose of a galactomannan, and an effective dose of a chemotherapeutic agent in a mixture. The formulation may further include a cancer therapeutic in which the formulation is in a powder form or in a liquid form.

DETAILED DESCRIPTION OF THE INVENTION

The following terms shall have the meanings indicated herein and in the claims, unless required otherwise by the context.

The term "subject" is defined here and in the claims as a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The term "patient" shall mean a human subject who has presented at a clinical setting with a particular symptom or symptoms suggesting the need for treatment.

The term "polysaccharide" refers to polymers comprised primarily of monomers of one or more sugars and substituted sugars. When isolated from nature, polysaccharide preparations comprise molecules that are heterogeneous in molecular weight.

"Efficacy" of a therapeutic agent refers to the relationship between a minimum effective dose and an extent of toxic side effects. Efficacy of an agent is increased if a therapeutic end point can be achieved by administration of a lower dose or a shorter dosage regimen. If toxicity can be decreased, a therapeutic agent can be administered on a longer dosage regimen or even chronically with greater patient compliance and improved quality of life. Further, decreased toxicity of an agent enables the practitioner to increase the dosage to achieve the therapeutic endpoint sooner, or to achieve a higher therapeutic endpoint.

The term "pharmaceutically acceptable carrier" refers to any and all solvents, dispersion media, e.g., human albumin or cross-linked gelatin polypeptides, coatings, antibacterial and antifungal agents, isotonic, e.g., sodium chloride or sodium glutamate, and absorption delaying agents, and the like that are physiologically compatible. The use of such media and agents for pharmaceutically active substances is well known in the art. Preferably, the carrier is suitable for oral, intravenous, intramuscular, subcutaneous, parenteral, spinal or epidural administration (e.g., by injection or infusion). Depending on the route of administration, the active compound can be coated in a material to protect the compound from the action of acids and other natural conditions that can inactivate the compound.

"Parenteral administration" includes but is not limited to administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The term "toxic" as used herein means any adverse effect caused by an agent when administered to a subject.

We provide a method of treating a subject with a therapeutic agent that minimizes the toxic side effects of the therapeutic agent. The method requires the co-administration of the agent with a polysaccharide. In addition to reducing toxicity, the co-administration of a polysaccharide with a therapeutic agent may increase the efficacy of the agent. In embodiments of the invention, the polysaccharide, galactomannan, has been shown to be effective in reducing the toxic side effects of therapeutic agents when coadministered with the agents. Although the examples provided herein describe the beneficial effects of galactomannans, we do not exclude the possibility that other polysaccharides may have a similar effect. The observed reduction in toxicity of a toxic therapeutic agent makes it possible to administer a greater dose without an increase in adverse side effects associated with treatment. The administration of increased dosages of a therapeutic agent having toxic side effects may be beneficial for treatment of a number of diseases including cancer, where the toxic side effects of traditional cytotoxic agents have limited their use.

In addition to reducing toxicity, efficacy may be enhanced by administering a therapeutic agent with a galactomannan. The increase in efficacy may arise from a synergistic effect between the galactomannan and the therapeutic agent mixture.

Both the polysaccharide and the agent may separately be formulated, in a dry form for example as a powder, or in a liquid form. In a preferred embodiment, the polysaccharide and therapeutic agent are mixed prior to administration. The mixture may be in the form of a liquid, a powder or an aerosol.

The dosage regimens for established therapeutic agents with known toxic side effects has been established and are described in the Physician's Desk Reference. For example, a description of adriamycin can be found in the Physician's Desk Reference 48$^{th}$ Edition (1994) pp 459–461 and for 5-FU on pages 1924–1925, these descriptions being incorporated by reference. The co-administration of polysaccharide with a therapeutic agent may utilize but is not limited to the dosage regimen and route of administration already established and approved for the therapeutic agent, the difference being the inclusion of the polysaccharide. For example, a single bolus can be administered, several divided doses can be administered over a period of time, or a dose can be proportionally reduced and administered over a time period by infusion, or can be increased, as indicated by the exigencies of the therapeutic situation. The dosage unit will be a mixture of polysaccharide with therapeutic agent. However we do not exclude the possibility that the polysaccharide and therapeutic agent could be administered sequentially as distinct formulations.

The formulation of the mixture may be derived from the standard formulation of the therapeutic agent to which the polysaccharide is added in a compatible solvent or as a powder. For example, the chemotherapeutic agent 5-FU is commonly formulated in an aqueous solution with excipients. In Example 1, aqueous galactomannan was added to the aqueous 5-FU to provide the formulation that was administered to the subject.

Pharmaceutically acceptable carriers are commonly added in typical drug formulations. For example in oral formulations, hydroxypropyl cellulose, colloidal silicon dioxide, magnesium carbonate, methacrylic acid copolymer, starch, talc, sugar sphere, sucrose, polyethylene glycol, polysorbate 80, and titanium dioxide: croscarmellose sodium, edible inks, gelatin, lactose monohydrate, magnesium stearate, povidone, sodium lauryl sulfate. carnuba wax, crospovidone, hydroxypropyl methylcellulose, lactose, microcrystalline cellulose, and other ingredients may be used. In addition, galactomannan has been used as a carrier for oral delivery of agents which are in a non-liquid form. (U.S. Pat. Nos. 4,447,337; 5,128,143; and 6,063,402).

One of ordinary skill in the art can determine and prescribe the effective amount of the therapeutic composition required based on clinical protocols. In general, a suitable daily dose of a composition of the invention will be that amount of the composition, which is the lowest dose effective to produce a therapeutic effect.

Embodiments of the invention demonstrate that administration of a mixture of a polysaccharide and a toxic therapeutic may result in reduced toxicity. An example of a polysaccharide with this activity is galactomannan. Galactomannan may be obtained from a variety of natural sources such as plants and may be made synthetically by enzymatic reactions or by chemical synthesis. Examples 1 and 2 show the effects of using galactomannans derived from two separate plant sources which have been demonstrated to be effective at reducing toxicity of therapeutic agents. In particular, Example 1 describes the use of galactomannan from a second plant species *Gelditsia triacanthos* and Example 2 describes the use of galactomannan obtained from the plant species *Medicago falcata*.

Galactomannan is a polymer that may occur in a variety of size ranges. Moreover, the galactomannan may be derivatized or hydrolyzed to result in fragments of the native molecule or may be reacted to provide chemically modified forms of the native molecule. Embodiments of the invention provide a galactomannan having a molecular weight in the range of 20,000–600,000 D. The galactomannan may further have a size in the range of 90–415,000 D or 40,000–200,000 D. Example 1 utilizes a galactomannan with an average molecular weight of 215,000 D while Example 2 utilizes a galactomannan with an average molecular weight of 83,000 D.

The ratio of mannose to galactose may vary according to the source of the galactomannan and the isolation procedure. In embodiments of the invention, the galactomannan may have a mannose to galactose ratio of 1.00–3.00, mannose: 0.3–1.5 galactose. The ratio of mannose to galactose may be 2.6:1.5 or 2.2:0.9 or 1.13:1 or 2.2:1. In Example 1, the ratio of mannose to galactose is 2.2:1 and in Example 2, the selected ratio of mannose to galactose in the galactomannan is 1.13:1.

The galactomannan may be provided with the therapeutic agent in a mixture at a ratio of 0.1:1 w/w to 10:1 w/w with the therapeutic agent. In Example 1, the ratio of galactomannan to 5-FU is 1:1.9 and in Example 2 the ratio of galactomannan to adriamycin is 1:0.6. The results shown in Examples 1 and 2 are unambigious with respect to the significant reduction in toxicity observed when chemotherapeutic agents are administered in the presence of galactomannan. In Example 1, the results are dramatic. Instead of a death rate of 3/5 mice with 5-FU with the surviving mice showing substantial lack of normal weight increase, the same dose administered with galactomannan results in 0/5 mice dying. All mice survive and the surviving mice have weights equivalent to control mice (treated with saline). The surviving mice appear normal in all aspects with no sign of toxicity. In Example 2, the results clearly demonstrate the advantages of formulating a mixture of adriamycin with galactomannan. Animals treated with an $LD_{50}$ dose of adriamycin according to standard toxicity tests result in a mortality of 3/5 mice. In contrast, when adriamycin is coadministered with adriamycin, the toxicity is reduced so that only 1/5 mice die. Moreover although there is some weight loss in the mice that survive, this weight loss is diminished.

In a preferred embodiment, the structure of galactomannans is a poly-__-1,4-mannan backbone, with the side substituents bound via ∀1,6-glycoside linkages, for example:

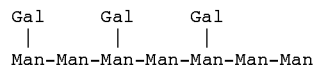

Without being bound by any particular theory, two possible mechanisms may account for the beneficial effect of galactomannan in a mixture with a toxic drug. One involves a direct physical interaction between the drug and galactomannan. For example, galactamannan may increase cancer cell membrane fluidity and permeability, as a result of galactose-specific interactions at the surface of the target cell. The polysaccharide can thus serve as an effective vehicle for delivery of the drug to the target. With respect to the treatment of cancer with chemotherapeutic agents, galactomannan may act to inhibit aggregation of tumor cells and their adhesion to normal cells, so that the cancer fails to metastasize. The toxicity of the chemotherapy drug may be reduced because the drug is inactive as long as it is bound to the polymer. Once the polymer drug conjugate enters the tumor, which galactomannan recognizes by virtue its structure and composition, galactomamman may release the anticancer drug. Another possible mode of action of galactomannan may involve its interaction with some regulatory sites in a biological system, particularly if those sites are governed by galactose-specific residues, such as galectins.

Use of the galactomannan containing formulation can have an immediate effect of increasing the responses of patients to the chemotherapy, for example, an effect is a decrease in the dosage of the agent required for effective chemotherapy, in the presence of the formulation. It will have an immediate effect by decreasing toxicity of the new drugs, and thereby improving a patient's quality of life.

The use of galactomannan administered in a mixture with a toxic agent can be applied to a wide range of agents and is restricted to anti-tumor or anti-cancer agents. These therapeutic areas include anti-depressants, anti-inflammatory agents, gastroenterology drugs (for treating ulcers and associated disorders), anti-psychotic drugs, anti-hyperlipidemic agents, etc. As many therapeutic agents must be administered as a chronic medicine, i.e., on a long-term basis, potential reduction in dosage and improvement in quality of life become significant factors in availability, cost of therapeutic agents, and patient compliance.

Examples of therapeutic agents with toxic side effects that may be administered with galactomannan to reduce their toxicity include the following: Anti-infectives including antibiotics, antivirals and vaccines, antineoplastics, cardiovascular drugs including antiarrythmics, antihypertensives etc., central nervous system drugs including analgesics, anorectics, anticonvulsants, anti-inflammatories and tranquilizers etc. OTICS, Opthalmics, gastrointestinal including anti-ulcer drugs, anticholinergic drugs etc. hormones, respiratory drugs including allergy medications, bronchodilators and decongestants, topical drugs and vitamins and minerals. Particular examples in the above categories are provided by way of illustration. Prilosec (AstraZeneca) described in U.S. Pat. No. 4,255,431 and Prevacid (TAP) described in U.S. Pat. No. 4,628,098; Lipitor (Pfizer) an anti-cholesterol drug described in U.S. Pat. No. 5,273,995. The antihyper-lipidemic agent, Zocor (Merck) U.S. Pat. No. 4,444,784; anti-depressants such as Prozac (Eli Lilly) described in U.S. Pat. No. 4,314,081; and Zoloft (Pfizer) described in U.S. Pat. No. 4,536,518; Paxil (SmithKline Beecham) U.S. Pat. Nos. 3,923,743 and 4,007,196; 4,721,723; antipsychotic agents such as Zyprexa (Eli Lilly) hematinic agents such as Epogen (Amgen), also known as Erythropoietin, and anti-inflammatory agents such as Celebrex (Searle). The formulations and dosages are provided in the Physicians Desk Reference.

The combination of toxic therapeutic agent together with galactomannan can be administered in any of the methods known in the art such as in a liquid formulation, tablet, suppository, gel, cream, transdermal or topical patch or aerosol. The formulation may be administered to a subject by any of the routes known in the art including by oral, mucosal, inhalation, or by parenteral administration as defined above.

All references cited herein are incorporated by reference. The following examples are provided by way of illustrating embodiments of the invention but are not intended to be limiting.

EXAMPLES

Example 1

Loss of Acute Toxicity of the Anti-Tumor Drug 5-FU in the Presence of Galactomannan Acute systemic toxicity of the anti-tumor drug 5-FU in the presence and absence of galactomannan was evaluated in Albino Swiss mice.

Albino Swiss mice (Harlan, Indianapolis, Ind.) were used as the experimental animals for measuring toxicity of therapeutic preparations following the ICH-Guideline on the Assessment of Systemic Exposure in Toxicity Studies, March 1995. Although this study was Non-GMP, it conformed to the guidelines set forth by the following references: The current FDA, 21 CFR, Part 58—Good Laboratory Practice for Nonclinical Laboratory Studies; AAALAC, "Guide for the Care and Use of Laboratory Animals," National Research Council, 1996. (NIH) (OPRR), "Public Health Service Policy on Humane Care and Use of Laboratory Animals," Health Research Extension Act of 1985 (Public Law 99–158 Nov. 20, 1985), Reprinted 1996; USDA, Department of Agriculture, Animal and Plant Health Inspection Service, 9 CFR Ch.1 (Jan. 1, 1995) edition, Subchapter A-Animal Welfare. ISO 10993-2, 1992. The Weight/Age range: 17.8–27.3 grams/ at least 34 days old (adult) weighed to nearest 0.1 gm. The mice were healthy, not previously used in other experimental procedures minimum 5 days under the same conditions as for the actual test. Animal room temperature: 68±5° F.

The animals were observed for clinical signs immediately after injection, and daily for the duration of the study. Observations conducted included all clinical and toxicologic signs. Animals were weighed prior to injection and at the end of the observation period. Animals surviving at the end of the study were sacrificed by carbon dioxide inhalation.

There were a total of 4 groups of 5 animals each. The groups were as follows: 1) NaCl (0.9%), 2) 5-FU (17 mg/ml), 3) GM (4.73 mg/ml) 4) 5-FU (17 mg/ml)+GM (9.06 mg/ml). The diluent in all cases was 0.9% NaCl. The test article solutions and NaCl (negative control) were injected intravenously via the tail vein at a dose of 0.5 ml/mouse.

The galactomannan which in nature has a molecular weight of about 800,000 D was cleaved to provide a galactomannan having an average molecular weight of 215,000 D. The galactomannan from this source has a galactose to mannan ratio of 2.2.

Galactomannan was isolated from *Gleditsia triacanthos*: (Honey locust, or Sweet-locust, or Thorny-locust) Fabaceae (family Leguminosae; Legume family, Bean family). Honey locust seeds, like those of many leguminous species, have impermeable coats and thus remain viable for long periods of time. Cleaned seeds average about 6,170/kg (2,800 lb), that is about 162 mg/seed (Vines, R.A. Trees, Shrubs, and Woody Vines of the Southwest. University of Texas Press, Austin, 1104 p (1960) Viability can be retained for several years when seeds are stored in sealed containers at 0° to 7° C. (32° to 45° F.) (Bonner, F. T., Burton, J. D., and Grigsby, H. C. Gleditsia L. Honeylocust. In Seeds of Woody Plants in the United States. P. 431–433. U.S. Department of Agriculture, Agriculture Handbook 450. Washington, D.C. 883 p. (1974)). The beans of some cultivars contain as much as 12 to 13% protein, and the pods contain up to 42% carbohydrates (Matoon, H. G. Farm Use for Tree Crops. Forest Leaves, 33, 5–7, 10–11 (1943); Stoutemyer, V. T., O'Rourke, F. L., and Steiner, W. W. Some Observations on the Vegetable Propagation of Honey Locust. J. Forestry 42, 32–36 (1944). Seeds were the primary source from which galactomannan was isolated.

Isolation, Purification, and Characterization of Galactomannan from *Gleditsia triacanthos*

(a) Disruption of Seeds.

Seeds were milled, and the obtained material (crude particles) was placed into 85% ethanol in a flask equipped with a condenser, at a ratio of 10 g of milled seeds to 100 ml of ethanol. The flask was placed into a water bath and the mixture was boiled for 45 min, to eliminate low-molecular weight carbohydrates and pigments. The settled (or filtered) material was washed with a small amount of 85% ethanol and air-dried.

(b) Water Extraction.

Approximately five volumes of water were added to the air-dried material, and the mixture was left for 6 to 10 hrs to swell. Then five more volumes of water were added, the mixture was homogenized in a blender, and then stirred continuously for 9 hours at room temperature. Some more water should be added during the homogenization and/or stirring, to make the final ratio of water and the initial dried material (w/w) equal to 40.

(c) Precipitation with Ethanol.

The mixture was centrifuged at 10,000 g for 30 min, the water extract was collected, the precipitate was washed with water under stirring and centrifuged again, and the washing-centrifugation procedure was repeated. All three water extracts were combined, the resulted volume was measured and recorded.

A 10 ml volume was taken, and mixed with 10 ml volume of 96% ethanol under stirring. Precipitation of a galactomannan is observed. The whole mixture was placed into refrigerator (4° C.) overnight, the precipitate was centrifuged, collected, and washed three times with 75% ethanol with the accompanying stirring and centrifugation. Liquid phases after each centrifugation were discarded. The final fibrous precipitate was air-dried and weighed. The yield of the galactomannan was within 20% to 26% of the weight of the initial seeds.

Since the final figure gives the yield of the galactomannan in 10 ml volume of the extract (see above), total amount of the galactomannan in the whole volume of the extract was calculated.

The precipitation/centrifugation procedure was repeated with the whole volume of the extract (less 10 ml removed in the preceding step), except the final air-drying was not complete, and the final material should be slightly wet. That is why a separate "calibration" isolation of galactomannan was needed, namely to calculate a total amount of the polysaccharide in the whole extract for the follow-up purification.

(d) Further Purification.

The wet galactomannan was dissolved in water, aiming at 10 mg/ml concentration. In order to reach such a concentration, the galactomannan was left to swell in water at 40°–50° C., and then the mixture was agitated using a homogenizer. To the resulting solution, a fresh Fehling reagent solution (see below) was added (at the ratio of 2–3 ml per 100 ml) under continuous stirring, to precipitate a galactomannan-$Cu^{+2}$ complex. At the end of the precipitation procedure, the mother liquor should be clear and slightly green-blue colored. An excess of the Fehling reagent solution should be avoided, since it can dissolve the forming precipitate.

The resulting precipitate was allowed to stay for 4 hours at room temperature. After the first hour, it is recommended to take an aliquot of the mother liquor and add a few drops of the Fehling reagent solution, in order to verify a completion of the precipitation. After 4 hours, the mixture was centrifuged, the precipitate was washed with cold water (at about 10° C.), and centrifuged again. The mother liquor was discarded.

To recover the galactomannan from its copper complex, the precipitate was transferred into a pre-cooled in a freezer and put on ice porcelain mortar, and a cold (10° C.) 5% hydrochloric acid in 96% ethanol (v/v) was added to cover the precipitate. The precipitate was sheared with a pestle to such an extent, that the material released had all the dye into the solution, and converted from gel back to a fibrous material. To facilitate the shearing process, if necessary, a little amount of solution of the acid in ethanol can be added.

Four volumes of 80% ethanol (per a volume of the precipitate) were added to the mixture in the mortar, and the resulting precipitate was isolated by centrifugation. It was washed 3 to 5 times with 80% ethanol, with a centrifugation after each washing (for a complete removal of copper salt), and air-dried for 1–2 hours.

The yield of the purified galactomannan was 13% to 18% from the weight of the initial seeds.

(e) Attenuation of the Molecular Weight.

The purified galactomannan was placed into a flask (equipped with a condenser, to be later used for boiling) and dissolved in water at concentration of 6–7 mg/ml. This can be achieved after swelling (at 45°–50° C.) and stirring of the material at this temperature. The pH of the resulting viscous solution was adjusted to 2.0–2.3, using 1N hydrochloric acid. The flask equipped with a condenser was placed onto a boiling water bath for 2 hours.

After hydrolysis, the liquid was filtered and collected, and the precipitate discarded. The liquid, that was a solution of a partially depolymerized galactomannan (DG), was neutralized with 1N NaOH to pH of 6.0–6.5, and the DG was precipitated with 1.5 volumes of 96% ethanol under continuous stirring. The precipitate and the mother liquor were placed in a refrigerator. The next day the precipitate was centrifuged, washed with 75% ethanol, and centrifuged again. The precipitate was washed with 85% ethanol, centrifuged, washed with 96% ethanol, and centrifuged again. The resulting partially depolymerized galactomannan precipitate was dried over $P_2O_5$. Its molecular weight was determined (in a separate experiment, the procedure see below) as 215,000 D, and mannose/galactose ratio was 2.2. Yield was 11% to 14% from weight of the initial seeds.

(f) Preparation of Fehling Reagent Solution.

The reagent solution consists of two solutions, A and B, in equal volumes.

Solution A: Dissolve in water 34.6 g of $CuSO_4$, add a few drops of $H_2SO_4$, and add water to the final volume of 500 ml.

Solution B: Dissolve in water 60 g of NaOH and 173 g of $KNaC_4H_4O_6 \times 4H_2O$, and add water to the final volume of 500 ml.

Solutions A and B are combined in equal volumes immediately before using Feling reagent solution. Solutions A and B can be safely stored for two years.

(g) Complete Acid Hydrolysis (for determination of Mannose/Galactose ratio in galactomannans).

5 mg of galactomannans were placed into a glass tube and 0.5 ml of 2N sulfuric acid was added. The tube was then fused and placed into a boiling water bath for four hours. The resulting solution was diluted with an equal volume of water, and neutralized to pH 5.5–6.0 (pH is monitored with a litmus paper) with anion exchangers Dowex-1 or Dowex-2 in their $HCO_3^-$ form. The solution was filtered, and the liquid was evaporated (e.g., using a rotor evaporator) to dryness.

(h) Determination of Mannose/Galactose Ratio in Galactomannans.

The dried acid hydrolyzate (see above) was mixed in a small flask with 1 ml of water and 25 mg of sodium borohydride, and left for 4–5 hours at room temperature for aldehyde groups of monosaccharides to be reduced. Then 1 ml of water was added, and the mixture was neutralized to pH 5.5–6.0 adding Dowex-50 in its $H^+$-form. The pH was monitored using litmus paper. The liquid was filtered, collected, and completely dried.

The dry residue was mixed with 1–2 ml of methanol, agitated by shaking, and dried (in order to remove boric acid as its volatile methyl ether derivative). This step was repeated two to three times, until the white residue of boric acid had disappeared. The flask then were placed into a vacuum desiccator for two hours, and the resulting sugar alcohols were acetylated as follows:

0.3 ml of water-free distilled pyridine and 0.3 ml of water-free distilled acetic anhydride were added into the flask with dried sugar alcohols, the flask was tightly closed using a ground glass stopper and placed into boiling water bath for 60–75 min. After it the flask is removed from the bath, carefully opened, and the reaction is stopped by addition of 1 ml of methanol. The resulting mixture of pyridine and acetic ester is evaporated at 30°–40° C. using a rotary evaporator. In order to facilitate the evaporation, 1–2 ml of methanol and 1–2 ml of heptane (in that order) should be added 2–3 times in the flask. The obtained dry residue is mixed with 0.2–0.5 ml of chloroform, and the resulting solution is injected into a gas-liquid chromatograph. As an option, chromatography columns packed with 5% XE 60 on chromatone N-AW can be used. A ratio of mannose to galactose is equal to a ratio of a relative area of their respective peaks, which are identified using pure mannose and galactose as calibration sugars.

(i) Viscosity of Galactomannan Solutions, and Molecular Weight of Galactomannan.

Relative viscosity of water solutions of galactomannan is determined using the Ostwald or Ubbelohde type viscometers, calibrated with water efflux times at 25° C. Efflux times for a series of concentrations of galactomannan in the range of 5.0 to 0.5 mg/ml are determined. Data obtained are calculated as follows:

$$\eta_{rel} = \tau/\tau^0,$$

where relative viscosity is equal to the ratio of efflux times for the galactomannan solution and water (at their equal volumes), and is determined at several galactomannan concentrations. For a series of galactomannan concentrations (C, mg/ml), specific viscosity is determined for each galactomannan concentration:

$$\eta_{sp}=\eta_{rel}-1,$$

and a graph of $\eta_{sp}/C$ from C, as well as in $\eta_{sp}/C$ from C is plotted. Both straight lines are extrapolated to the zero concentration of galactomannan (C=0), giving the intrinsic viscosity [η] of the galactomannan.

Molecular weight of the galactomannan is calculated from its intrinsic viscosity as $$[\eta]=0.168\times DP^{0.98},$$

where DP is degree of polymerization. Since the "molecular weight" of a single repetitive unit in galactomannan is 162, molecular weight (MW) of the galactomannan is MW=162×DP.

The galactomannan was found to have increased solubility in a solution containing 5-FU. The 5-FU was formulated for intravenous injection at the concentration and pH provided for in the Physician's Desk Reference.

A single dose intravenous injection of the 5-FU alone or 5-FU together with galactomannan preparations was provided via the tail vein at a dose of 0.5 ml/mouse at the doses described below in (1)–(4) and observed for clinical signs immediately after injection, and daily for the duration of the study.

There were a total of 3 groups of 5 animals each. The groups were as follows: 1) 0.9% NaCl only, 2) 5-FU only (17 mg/ml) 3) GM (4.73 mg/ml) and 5-FU (17 mg/ml)+GM (9.06 mg/ml).

The dose of 5-FU was 20% above $LD_{50}$ i.e. 420 mg/kg compared with 340 mg/kg for an $LD_{50}$.

0.9% NaCL was used as a diluent. Animals were weighed prior to injection and at the end of the observation period. Animals surviving at the end of the study were sacrificed by carbon dioxide inhalation.

As the 5-FU was injected intravenously at the $LD_{50}$ dose, mortality was expected in 50% of the animals. The ability of the galactomannan to reduce the toxicity of $LD_{50}$ dose of 5-FU was measured by presence or absence of mortality in animals injected with the combination of 5-FU and galactomannan.

TABLE 1

| Group | Animal # | Body Weight (g) Day 0 Jan. 9, 2001 | Day 17 Jan. 26, 2001 | Weight Change | Signs of Toxicity # |
|---|---|---|---|---|---|
| NaCl | 1 | 19.0 | 26.2 | 7.2 | None |
|  | 2 | 22.1 | 24.8 | 2.7 | None |
|  | 3 | 21.6 | 25.4 | 3.8 | None |
|  | 4 | 18.7 | 25.3 | 6.6 | None |
|  | 5 | 17.5 | 24.9 | 7.4 | None |
| 5-FU | 6 | 20.4 | 22.1 | 1.7 | L, P |
|  | 7 | 20.6 | * | — | D |
|  | 8 | 19.4 | * | — | D |
|  | 9 | 22.5 | 24.0 | 1.5 | L, P |
|  | 10 | 21.2 | * | — | D |
| GM | 21 | 18.4 | 22.4 | 4.0 | None |
|  | 22 | 21.7 | 26.3 | 4.6 | None |
|  | 23 | 20.4 | 25.2 | 4.8 | None |
|  | 24 | 22.6 | 27.1 | 4.5 | None |
|  | 25 | 22.5 | 27.5 | 5.0 | None |
| 5-FU/GM | 41 | 19.8 | 26.8 | 7.0 | None |
|  | 42 | 20.8 | 25.9 | 5.1 | None |
|  | 43 | 20.3 | 27.1 | 6.8 | None |
|  | 44 | 18.8 | 24.9 | 6.1 | None |
|  | 45 | 22.4 | 27.5 | 5.1 | None |

Summary of clinical observations.
*toxicity observed. Animals died before the end of the study.
L - lethargy, P - piloerection, D - death. All of the mice were male.

The in-life portion of this acute systemic toxicity test was originally 14 days. However, the first mortality was observed on day 13. Thus the in-life duration of the study was extended to 17 days.

Animals injected with NaCl alone, or the polysaccharides alone did not show any signs of toxicity and all the animals survived to the end of the study. All the animals gained weight by the end of the study. Moreover, no signs of toxicity or mortality were observed in the animals injected with 5-FU and GM where the animals gained weight similar to the controls. This result was in marked contrast to the results in mice treated with 5-FU.

Example 2

Loss of Acute Toxicity of the Anti-Tumor Drug Adriamycin in the Presence of Galactomannan Acute systemic toxicity of the anti-tumor drug adriamycin in the presence and absence of galactomannan was evaluated in Albino Swiss mice. Mice were bred as described in Example 1. Experimental procedures followed approved governmental guidelines as described in Example 1.

The galactomannan was derived from *Medicago falcata*. The isolated galactomannan was cleaved to obtain a preparation with an average molecular weight of 83,000 D. The ratio of galactose to mannose for this preparation was 1.13. Galactomannan was isolated from *Medicago falcata* as follows:

Isolation, Purification, and Characterization of Biologically Active Galactomannan from *Medicago falcata* (Lucerne).

Seeds were the primary source of the galactomannan that was isolated from *Medicago falcata* in this study.

(a) Disruption of seeds (as in Example 1)
(b) Benzene Treatment

The dried material was mixed with 3× volume of distilled benzene, and the mixture was periodically stirred for about 45 min. The material was filtered, washed with a small amount of distilled benzene, and air-dried.

(c) Water Extraction (as in Example 1)
(d) Precipitation with Ethanol

The mixture was centrifuged at 10,000 g for 30 min, the water extract was collected, the precipitate was washed with water under stirring and centrifuged again, and the washing-centrifugation procedure was repeated. All three water extracts were combined, and concentrated four-fold at 60°–65° C. using a rotor evaporator. The resulted volume was centrifuged at 5,000 rpm for 60 min for removal of proteins, which were coagulated at the bottoms of centrifuge vessels. The resulted volume was measured and recorded.

A 5 ml volume was taken, and mixed with 5 ml volume of 96% ethanol under stirring. Precipitation of a galactomannan was observed. The whole mixture was placed into refrigerator (4° C.) overnight, the precipitate was centrifuged, collected, and washed three times with 75% ethanol with the accompanying stirring and centrifugation. Liquid phases after each centrifugation were discarded. The final fibrous precipitate was air-dried and weighed. The yield of the galactomannan should be within 6% to 8% of the weight of the initial seeds.

Since the final figure gives the yield of the galactomannan in 5 ml volume of the extract (see above), total amount of the galactomannan in the whole volume of the extract was calculated.

The precipitation/centrifugation procedure was repeated with the whole volume of the extract (less 5 ml removed in the preceding step), except the final air-drying was not complete, and the final material should be slightly wet. That is why a separate "calibration" isolation of galactomannan was needed, namely to calculate a total amount of the polysaccharide in the whole extract for the follow-up purification.

(e) Further Purification (see Example 1)

The yield of the purified galactomannan should be 6.5% from the weight of the initial seeds.

(f) Preparation of Fehling Reagent Solution as in Example 1.

(g) Preparation of Dowex resins.

Dry resins are left in water overnight for swelling, then a swollen resin is placed on glass filter and the respective water solutions are passed through. For Dowex-1 to be charged to its anionic form, 4% sodium bicarbonate solution is slowly passed through, and then the resin is washed with water until passing through water has the neutral pH (monitored with litmus paper). For Dowex-50 to be charged to its cationic ($H^+$) form, 3–4 volumes of 1 N hydrochloric acid is passed through, and then the resin is washed with water as described above until pH of water is neutral.

(h) Complete Acid Hydrolysis (as in Example 1).

(i) Determination of Mannose/Galactose Ratio in Galactomannans (see Example 1)

(j) Viscosity of Galactomannan Solutions, and Molecular Weight of Galactomannan (see Example 1).

The galactomannan was found to have increased solubility in a solution containing adriamycin A. The adriamycin was formulated for intravenous injection at the concentration and pH provided for in the Physician's Desk Reference.

A single dose intravenous injection of the adriamycin alone or adriamycin together with galactomannan preparations was provided via the tail vein at a dose of 0.5 ml/mouse at the doses described below in (1)–(3) and observed for clinical signs immediately after injection, and daily for the duration of the study.

There were a total of 3 groups of 5 animals each. The groups were as follows: 1) 0.9% NaCl only, 2) Adriamycin only (1.1 mg/ml) and Adriamycin (1.1 mg/ml)+GM (7.2 mg/ml). $LD_{50}$ for Adriamycin (i.v. in mice) is 21.1 mg/kg (The Merck Index, $12^{th}$ Edition, p 582).

0.9% NaCL was used as a diluent. Animals were weighed prior to injection and at the end of the observation period. Animals surviving at the end of the study were sacrificed by carbon dioxide inhalation.

As the Adriamycin was injected intravenously at the $LD_{50}$ dose, mortality was expected in 50% of the animals. The ability of galactomannan to reduce the toxicity of $LD_{50}$ dose of Adriamycin was measured by presence or absence of mortality in animals injected with the combination of Adriamycin and the particular polysaccharide.

Results

Animals injected with NaCl alone did not show any signs of toxicity and all the animals survived to the end of the study. All the animals gained weight by the end of the study.

Three out of 5 animals in the Adriamycin alone group (one animal each on day 1, day 4 and day 5) died before the end of the study. The surviving 2 animals lost weight by the end of the study (Table I).

One out of 5 animals injected with Adriamycin and GM (one animal on day 4) died before the end of the study. Three out of four remaining animals lost weight by the end of the study. The fourth animal gained very little weight (Table I). Observations conducted included all clinical and toxicologic signs. Adriamycin only at the $LD_{50}$ dose caused death in 3 out of 5 mice. However, mice injected with the combination of GM and a $LD_{50}$ dose of Adriamycin resulted in the death of only one mouse demonstrating that GM has the ability to decrease the toxicity of the anti-tumor drug Adriamycin.

TABLE 2

Effect of Galactomannan (GM) when co-administered with Adriamycin

| Group | Animal # | Body Weight (g) Day 0 Feb. 05, 2001 | Day 14 Feb. 19, 2001 | Weight Change | Signs of Toxicity # |
|---|---|---|---|---|---|
| NaCl | 1 | 21.8 | 26.0 | 4.2 | None |
|  | 2 | 17.8 | 30.2 | 12.4 | None |
|  | 3 | 27.0 | 29.9 | 2.9 | None |
|  | 4 | 23.6 | 27.5 | 3.9 | None |
|  | 5 | 25.7 | 33.2 | 7.5 | None |
| Adriamycin | 6 | 27.3 | 25.2 | -2.1 | None |
|  | 7 | 22.7 | 19.1 | -3.6 | None |
|  | 8 | 21.0 | * | — | D |
|  | 9 | 25.2 | * | — | D |
|  | 10 | 21.6 | * | — | D |
| Adriamycin/GM | 16 | 25.3 | * | — | D |
|  | 17 | 25.1 | 23.2 | -1.9 | None |
|  | 18 | 25.8 | 24.2 | -1.6 | None |
|  | 19 | 24.7 | 23.7 | -1.0 | None |
|  | 20 | 24.5 | 25.6 | 1.1 | None |

Summary of clinical observations.
*toxicity observed. Animals died before the end of the study.
D = death. Male animals were used throughout the study.

What is claimed is:

1. A cancer therapeutic formulation having reduced toxicity, comprising, an effective dose of a galactomannan, and an effective dose of a chemotherapeutic agent in a mixture.

2. A cancer therapeutic formulation according to claim 1 wherein the formulation is in a powder form.

3. A cancer therapeutic formulation according to claim 1 wherein the formulation is in a liquid form.

4. A pharmaceutical formulation, comprising: a mixture of galactomannan polysaccharide and an effective dose for treating cancer of a chemotherapeutic agent in a pharmaceutically acceptable formulation.

5. The pharmaceutical formulation of claim 4, wherein the mixture comprises an amount of galactomannan and the chemotherapeutic agent in the ratio suitable for reducing a toxic effect in the subject, the toxic effect resulting from administration of a cancer treating amount of chemotherapeutic agent absent galactomannan.

6. The pharmaceutical formulation of claim 4, wherein the mixture comprises an amount of galactomannan and the chemotherapeutic agent in a ratio suitable for enhancing efficacy of chemotherapeutic effect for treating the cancer.

7. The pharmaceutical formulation of claim 4, wherein the chemotherapeutic agent is 5-FU.

8. The pharmaceutical formulation of claim 4, wherein the chemotherapeutic agent is adriamycin.

9. The formulation of claim 5 or 6, wherein the formulation is in a powder form.

10. The formulation of claim 5 or 6, wherein the formulation is in a liquid form.

* * * * *